United States Patent
Parkinson et al.

(10) Patent No.: US 7,037,311 B2
(45) Date of Patent: May 2, 2006

(54) TOOL FOR GRIPPING AN ORTHOPEDIC IMPLANT

(75) Inventors: Fred W. Parkinson, Warsaw, IN (US); Christine L. Douglas, Fort Wayne, IN (US); Justin S. Hertzler, Warsaw, IN (US); Stephen H. Hoag, Warsaw, IN (US); Kyle A. Bohnenkamper, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 492 days.

(21) Appl. No.: 10/194,874

(22) Filed: Jul. 12, 2002

(65) Prior Publication Data

US 2004/0010262 A1    Jan. 15, 2004

(51) Int. Cl.
*A61B 17/58* (2006.01)
(52) U.S. Cl. ......................................................... 606/99
(58) Field of Classification Search ............... 606/73, 606/81, 86, 91, 99, 104, 72
See application file for complete search history.

(56) References Cited

U.S. PATENT DOCUMENTS

| | | | | |
|---|---|---|---|---|
| 3,801,989 A | * | 4/1974 | McKee | ..................... 623/22.12 |
| 4,677,972 A | | 7/1987 | Tornier | |
| 4,813,962 A | | 3/1989 | Deckner et al. | |
| 4,919,679 A | | 4/1990 | Averill et al. | |
| 5,020,519 A | * | 6/1991 | Hayes et al. | ................ 606/237 |
| 5,064,427 A | | 11/1991 | Burkinshaw | |
| 5,169,399 A | * | 12/1992 | Ryland et al. | ................. 606/91 |
| 5,190,549 A | * | 3/1993 | Miller et al. | ................... 606/85 |
| 5,409,492 A | | 4/1995 | Jones et al. | |
| 5,514,136 A | | 5/1996 | Richelsoph | |
| 5,531,750 A | * | 7/1996 | Even-Esh | ..................... 606/79 |

(Continued)

FOREIGN PATENT DOCUMENTS

FR    2 615 097    11/1988

(Continued)

OTHER PUBLICATIONS

Drawing sheet (1) illustrating gripping tool for orthopaedic implant believed to be in public use or on sale in the U.S. at least as early as Aug., 1993, Serial #: 10/194,744.

*Primary Examiner*—David O. Reip
*Assistant Examiner*—Richard Shaffer
(74) *Attorney, Agent, or Firm*—Baker & Daniels LLP; Jonathan Feuchtwang

(57) ABSTRACT

A tool for gripping an orthopedic implant having a recess. The tool includes a plurality of engagement members which extend freely from the tool body to their free ends. An elongate biasing member having a radially enlarged portion at its distal end is positioned along a central axis of the tool with its radially enlarged portion positioned between the engagement members. Axial translation of the biasing member biasingly engages the radially enlarged portion with the engagement members and resiliently deflects the engagement members from a contracted position to an expanded position. The engagement members are insertable into a recess in the implant when in the contracted position and outward biasing of the engagement members firmly secures the implant to the tool. The use engagement members which define a non-circular cross sectional shape and a correspondingly shaped recess in the implant inhibits relative rotational movement between the tool and implant.

11 Claims, 3 Drawing Sheets

U.S. PATENT DOCUMENTS

| | | | |
|---|---|---|---|
| 5,540,697 A * | 7/1996 | Rehmann et al. | 606/91 |
| 5,571,111 A * | 11/1996 | Aboczky | 606/91 |
| 5,720,753 A * | 2/1998 | Sander et al. | 606/104 |
| 5,782,830 A | 7/1998 | Farris | |
| 5,849,015 A | 12/1998 | Haywood et al. | |
| 5,919,194 A * | 7/1999 | Anderson | 606/72 |
| 5,928,244 A * | 7/1999 | Tovey et al. | 606/104 |
| 5,954,727 A * | 9/1999 | Collazo | 606/91 |
| 6,113,605 A | 9/2000 | Storer | |
| 6,342,057 B1 * | 1/2002 | Brace et al. | 606/96 |
| 6,599,295 B1 * | 7/2003 | Tornier et al. | 606/104 |

FOREIGN PATENT DOCUMENTS

GB      2 307 861      11/1997

\* cited by examiner

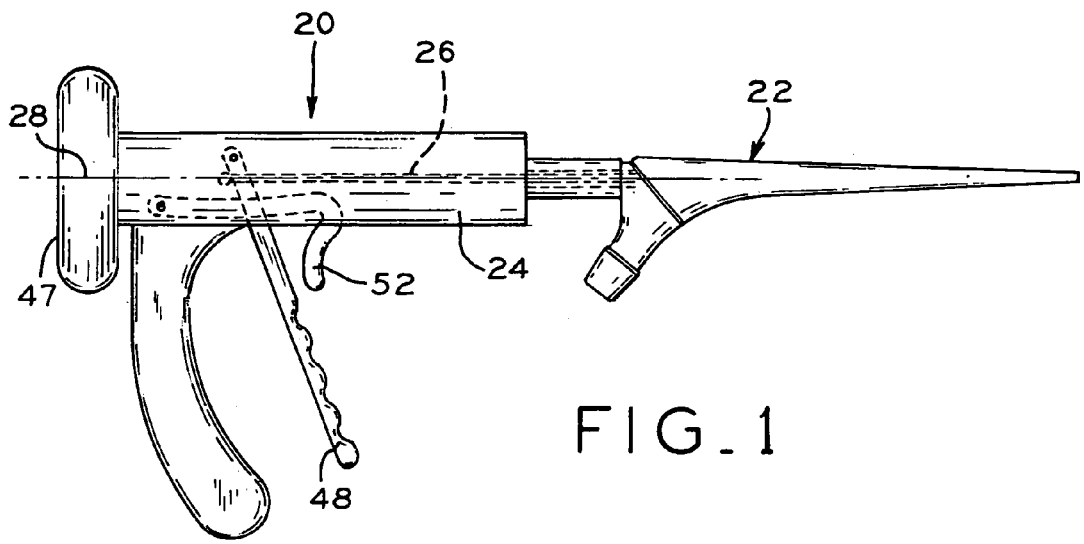
FIG.1
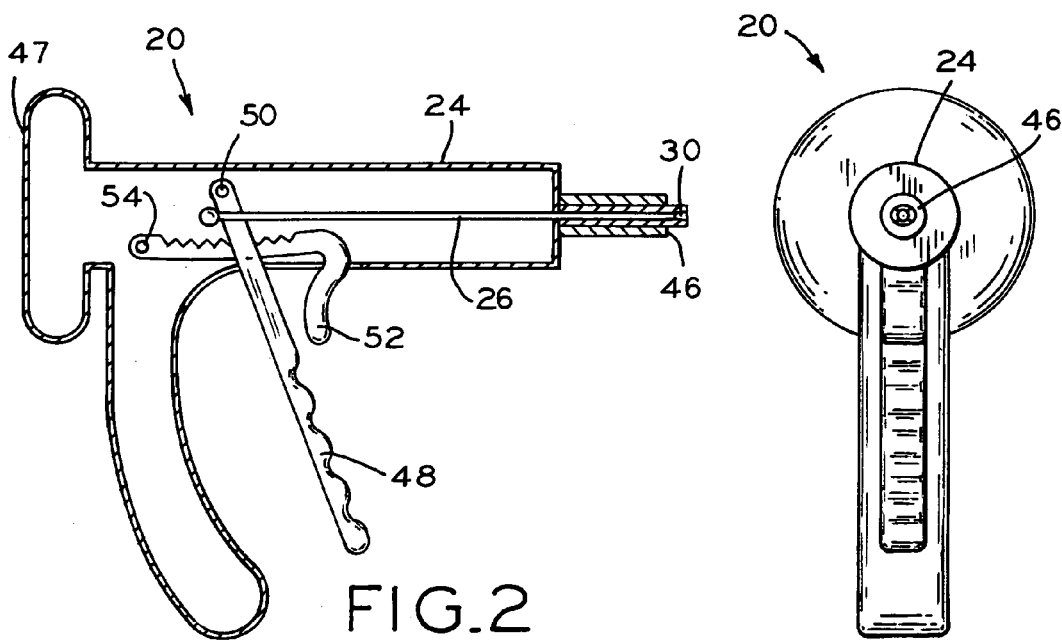
FIG.2
FIG.3
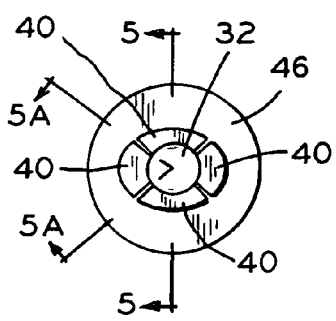
FIG.4
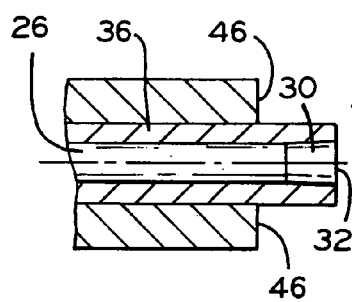
FIG.5
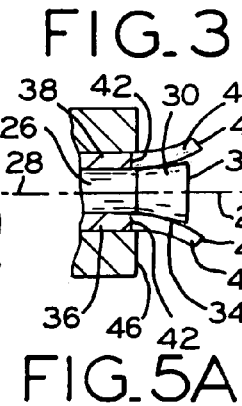
FIG.5A

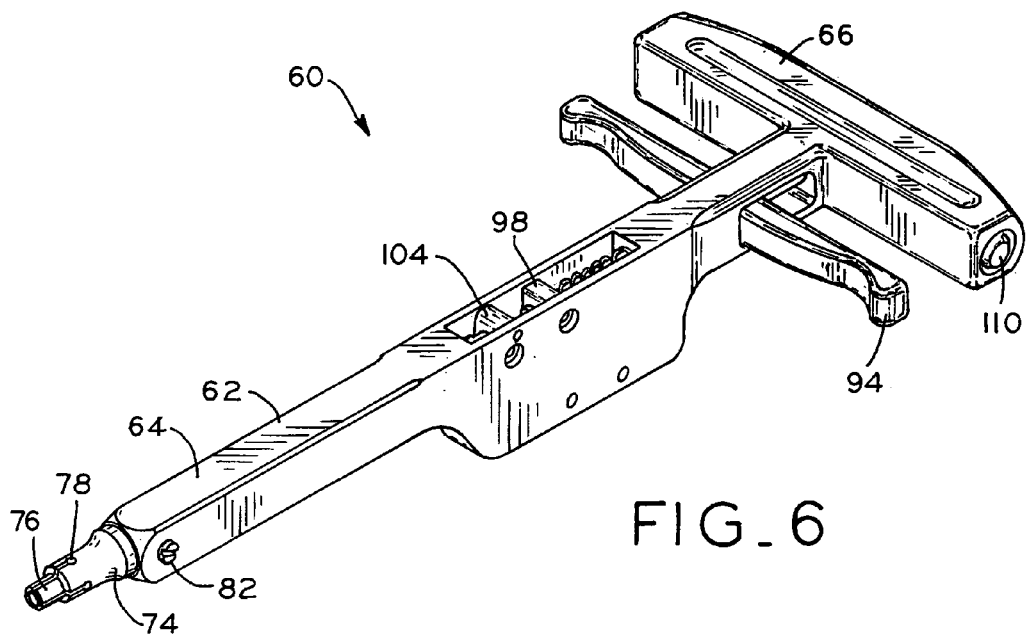
FIG_6
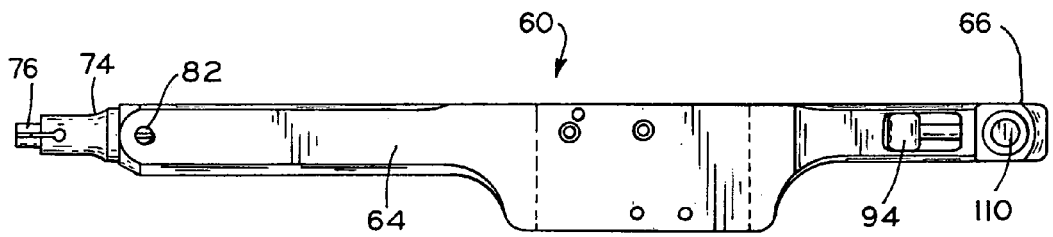
FIG_7
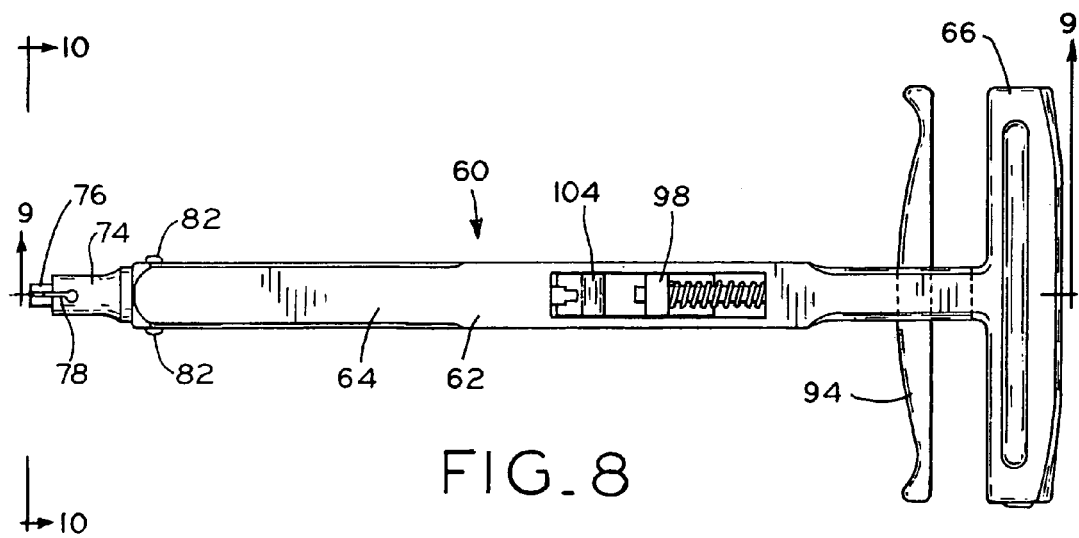
FIG_8

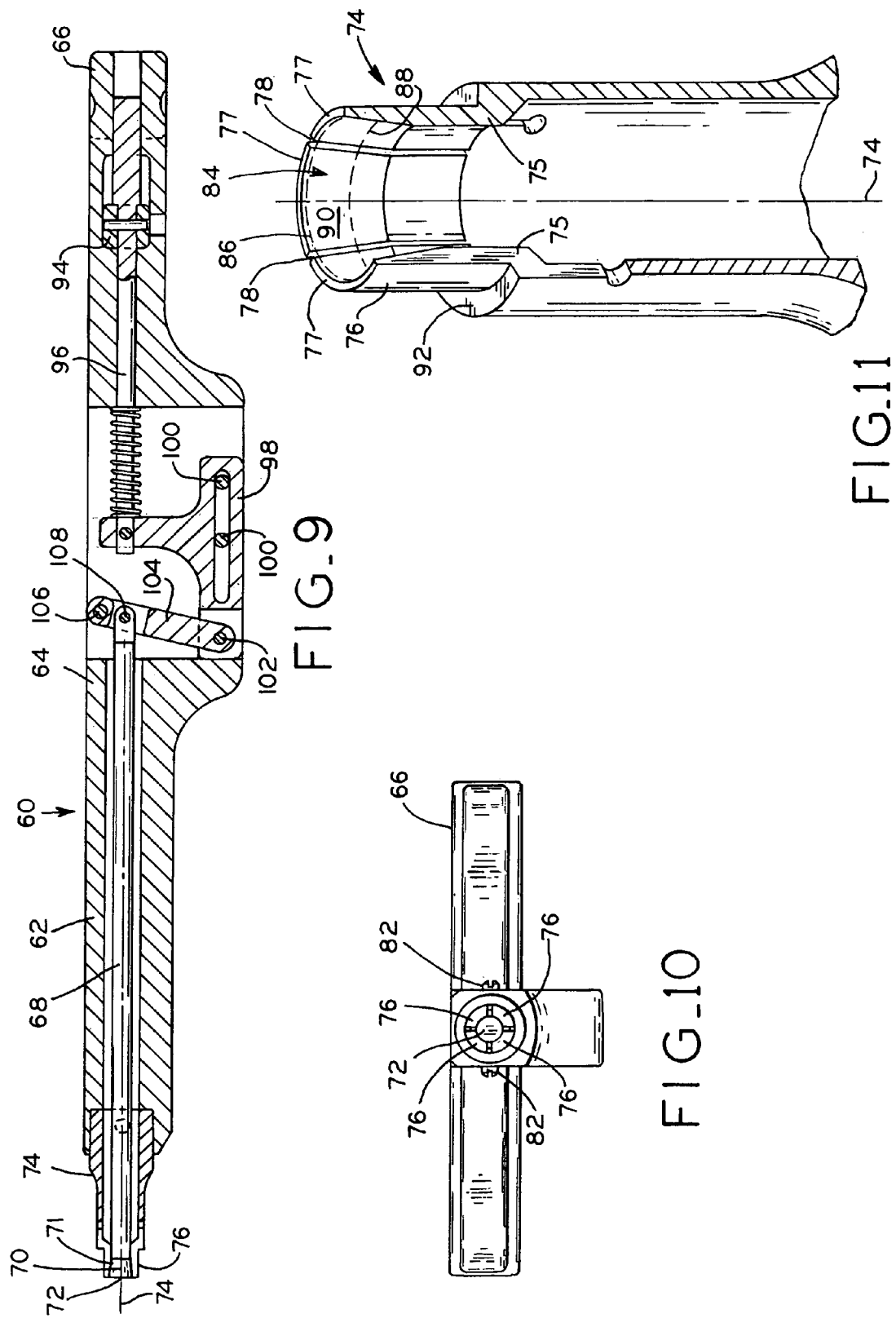

TOOL FOR GRIPPING AN ORTHOPEDIC IMPLANT

BACKGROUND OF THE INVENTION

1. Field of the Invention

The present invention relates to instrumentation for use with orthopedic implants and, more particularly, to a tool for gripping and inserting an orthopedic implant such as a femoral stem prosthesis.

2. Description of the Related Art

A femoral stem prosthesis, and other long bone prostheses, generally include an elongated stem which is inserted into the intramedullary canal of the long bone after the canal has been prepared to receive the prosthesis. The prosthesis must be gripped to properly insert and position the stem of the prosthesis in the prepared canal. Relative movement between the tool used to grip the prosthesis and the prosthesis is undesirable during the insertion procedure since such relative motion could have a negative impact on the proper positioning of the prosthesis within the canal. It is also undesirable for the tool to grip the prosthesis in a manner that might scratch or otherwise damage the prosthesis, potentially rendering the prosthesis unusable. Once the prosthesis has been properly positioned within the bone, the gripping tool must be released. During the release of the gripping tool from the prosthesis it is undesirable for the releasing action to impart any relative motion between the prosthesis and the bone in which the prosthesis has been properly positioned. For such prostheses which are cemented within the intramedullary canal, releasing the prosthesis without imparting any relative movement between the implant and the surrounding cement mantle and thereby avoid disturbing the bond between the implant and cement is of particular importance.

SUMMARY OF THE INVENTION

The present invention provides a tool for gripping an orthopedic prosthesis or implant which enables the tool to firmly grip the implant in a manner which is not likely to damage the implant and allows the tool to be released from the implant after its insertion in a bone in a manner which is unlikely to disturb the proper positioning of the implant relative to the bone.

The invention comprises, in one form thereof, a tool for gripping an orthopedic implant having a recess which includes a tool body and a plurality of engagement members circumferentially disposed about a central axis, each of the engagement members having a fixed end secured to the tool body and extending freely to an opposite free end. The plurality of engagement members have a contracted position wherein each of the engagement members extend from their fixed ends to their free ends in a direction substantially parallel to the central axis. The plurality of engagement members also have an expanded position wherein at least one of the engagement members is resiliently deflected with the free end of the at least one engagement member displaced radially outwardly relative to the central axis, the fixed ends of the engagement members remaining in the same position relative to the tool body in both the contracted and expanded positions. The tool also includes a biasing member which is biasingly engageable with the at least one engagement member wherein engagement of the biasing member with the at least one engagement member outwardly deflects the at least one engagement member and places the plurality of engagement members in their expanded position. The plurality of engagement members are adapted for insertion into the recess of the implant when they are in their contracted position and movement of the engagement members into their expanded position when located in the recess firmly engages the plurality of engagement members with the implant and secures the implant to the tool.

The biasing member may take the form of an elongate member having a radially enlarged portion at one end with the biasing member disposed along the central axis and its radially enlarged portion disposed between the engagement members. Positioning a distal end of the radially enlarged portion proximate the free ends of the engagement members places the engagement members in their contracted position and movement of the distal end towards the fixed ends biasingly engages the radially enlarged portion with the engagement members and resiliently deflects each of the engagement members whereby each of the free ends is displaced radially outwardly and the elongate members are placed in their expanded position.

The invention comprises, in another form thereof, a tool for gripping an orthopedic implant having a recess which includes a tool body and a plurality of engagement members which are circumferentially adjacently disposed about a central axis. Each of the engagement members has a fixed end secured to the tool body and extend freely to an opposite free end. The plurality of engagement members have a contracted position wherein each of the engagement members extend substantially parallel to the central axis. The plurality of engagement members also have an expanded position wherein each of the engagement members is resiliently deflected with each of the free ends displaced radially outwardly relative to the central axis. The tool also includes a biasing member which is moveable relative to the plurality of engagement members from a first position wherein at least a portion of the biasing member is disposed along the central axis at a first axial location with the plurality of engagement members in their contracted position to a second position wherein the biasing member is engaged with the plurality of engagement members and resiliently deflects the plurality of engagement members into their expanded position. The plurality of engagement members are adapted for insertion into the recess of the implant when in their contracted position and movement of the plurality of engagement members into their expanded position when located in the recess firmly engages the plurality of engagement members with the implant and secures the implant to the tool.

The biasing member may take the form of an elongate member which is disposed along the central axis and has a radially enlarged portion. Movement of the biasing member from the first position to the second position includes the axial translation of the radially enlarged portion and biasing engagement of the radially enlarged portion with the plurality of engagement members. The plurality of engagement members may also define a central opening having a first inner circumference at a first axial position and a second inner circumference at a second axial position wherein the first inner circumference is larger than the second inner circumference. The radially enlarged portion of the biasing member is axially disposed proximate the first axial position of the engagement members when the engagement members in the contracted position and the biasing member is in its first position. The radially enlarged portion of the biasing member engages the plurality of engagement members at their second axial position when the engagement members are in their expanded position and the biasing member is in its second position.

The engagement members may also be configured whereby each of the engagement members define a portion of a first inclined surface extending from the first inner circumference to the second inner circumference with the radially enlarged portion defining a second inclined surface. The first and second inclined surfaces face opposite directions and are positioned at a common angle to the central axis. At least a portion of the first and second inclined surfaces are adjacently positioned when the biasing member is in its first position and the engagement members are in the contracted position. Movement of the biasing member to the second position biasingly engages the first and second inclined surfaces and thereby deflects the engagement members into their expanded position.

The different forms of the tool in accordance with the present invention may also include a plurality of engagement members which each include a fixed end integrally formed with a collar portion of a single integral part wherein the collar portion encircles the central axis and is secured to the tool body. The tool may also include an impact surface disposed proximate the engagement members and adapted to transfer an impact force to the implant when the plurality of engagement members have secured the implant to the tool. Such an impact surface may be disposed on the collar portion described above which thereby inhibits relative rotational movement between the tool and the implant.

The different forms of the tool in accordance with the present invention may also include a plurality of engagement members which define a non-circular cross sectional shape when in the contracted position.

An advantage of the present invention is that it provides a tool which firmly grips the implant in a manner which is not likely to damage the implant.

Another advantage of the present invention is that it provides a tool which has a mechanism for releasing the tool from the implant after its insertion in a bone which is unlikely to disturb the proper positioning of the implant relative to the bone.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 1 is a schematic view of a first embodiment of a tool in accordance with the present invention attached to a femoral prosthesis.

FIG. 2 is a cut away view of the first embodiment.

FIG. 3 is a end view of the first embodiment.

FIG. 4 is a detail end view of the distal end of the first embodiment.

FIG. 5 is a partially sectional view of the distal end of the first embodiment in a contracted position.

FIG. 5A is a partially sectional and cut away view of the distal end of the first embodiment in an expanded position.

FIG. 6 is a perspective view of a second embodiment of a tool in accordance with the present invention.

FIG. 7 is a side view of the second embodiment.

FIG. 8 is a top view of the second embodiment.

FIG. 9 is a sectional view of the second embodiment taken along line 9—9 of FIG. 8.

FIG. 10 is an end view of the second embodiment.

FIG. 11 is a partial cut away view of the engagement members and collar portion of the second embodiment.

Corresponding reference characters indicate corresponding parts throughout the several views. Although the exemplification set out herein illustrates embodiments of the invention, in multiple forms, the embodiments disclosed below are not intended to be exhaustive or to be construed as limiting the scope of the invention to the precise forms disclosed.

DESCRIPTION OF THE PRESENT INVENTION

A first embodiment of a tool 20 in accordance with the present invention is schematically illustrated in FIGS. 1–5A. A femoral stem prosthesis 22 having a smooth walled recess or bore is shown attached to the tool in manner which is explained in greater detail below.

Tool 20 includes a tool body 24 and a biasing member 26 which takes the form of an elongate member disposed along central axis 28. Biasing member 26 includes a radially enlarged portion 30 located at its distal end 32. Radially enlarged portion 30 is defined by an inclined surface 34 which tapers outwardly as it extends towards distal end 32. A collet 36 is located on the distal end of tool 20. Collet 36 takes the form of a single integral part which includes a collar portion 38 which encircles central axis 28 and a plurality of fingers or engagement members 40. Tool 20 can be manufactured out of stainless steel or other suitable materials using conventional manufacturing techniques.

As can be seen with reference to FIGS. 4 and 5A, engagement members 40 each have a fixed end 42 where each member 40 is secured to tool body 24. In the embodiment of FIGS. 1–5A, fixed ends 42 are integrally joined to collar portion 38 which in turn is secured to the remainder of tool body 24 thereby securing fixed ends 42 to tool body 24. Engagement members 40 extend freely from fixed ends 42 to free ends 44.

Engagement members 40 have a contracted position shown in FIGS. 4 and 5 wherein each of the engagement members 40 extend from their fixed end 42 to their free end 44 in a direction substantially parallel to central axis 28. Biasing member 26 is disposed along central axis 28 with radially enlarged portion 30 disposed at a first axial position between engagement members 40 with distal end 32 located proximate free ends 44 when engagement members 40 are in the contracted position.

In this position, engagement members 40 can be inserted into an opening or recess in implant 22 which generally corresponds to the shape of engagement members in their contracted position. Engagement members 40 are inserted into the opening in implant 22 until impact surface 46 bears against implant 22 adjacent the recess into which members 40 are inserted. Tool 20 is then secured to implant 22 by axially retracting biasing member 26 along central axis 28 towards fixed ends 42. As biasing member 26 and radially enlarged portion 30 is axially translated from the position shown in FIG. 5 to the position shown in FIG. 5A, radially enlarged portion 30 biasingly engages engagement members 40 and outwardly deflects engagement members 40 placing engagement members 40 into an expanded position as shown in FIG. 5A.

In the expanded position shown in FIG. 5A, engagement members 40 are resiliently deflected outwardly with free ends 44 displaced radially outwardly relative to central axis 28. Fixed ends 42 are not moved relative to tool body 24 by the outward deflection of engagement members 40. The outward deflection of engagement members 40 into an expanded position firmly engages members 40 with the inner surface of the implant recess and secures implant 22 to tool 20. Although in the illustrated embodiments each of the engagement members 40 are outwardly deflectable, alternative embodiments could employ stationary engagement members provided that at least one of the engagement members was outwardly deflectable with its free end being outwardly radially displaceable to provide for the engagement of the engagement members with the inner surface of the implant recess.

After implant 22 has been secured to tool 20 it can be inserted into the prepared intramedullary canal of a femur. The insertion of the implant 22 may require the application of force such as through the impact of a mallet or slap hammer. Such impact forces may be applied to rear surface 47 of tool body 24 and transferred to implant 22 via impact surface 46 after engagement members 40 have secured the implant 22 to tool 20. As can be seen in FIGS. 4 and 5, impact surface 46 is positioned substantially transverse to central axis 28 and located proximate engagement members 40.

As can be seen in FIG. 4, engagement members 40 are circumferentially adjacently disposed about central axis 28 and define a cross sectional shape which is arcuate and non-circular. When both the recess of implant 22 and the engagement members 40 of tool 20 have non-circular cross sectional shapes, the rotational orientation of implant 22 to tool 20 can be controlled and relative rotational movement between implant 22 and tool 20 can be inhibited.

FIGS. 1 and 2 schematically illustrate a ratcheting mechanism which may be used to retract biasing member 26 and secure biasing member 26 in its retracted position. The mechanism includes a lever element 48 which is pulled rearwardly and pivots about pivot pin 50. As lever 48 moves rearwardly it is captured in teeth located on geared trigger 52 which pivots about pivot pin 54 and is biased upwardly by a spring (not shown) or similar biasing element. Teeth on trigger 52 prevent the forward movement of lever 48 and biasing member 26 which is secured thereto. To release lever 48, and biasing member 26, trigger 52 is pulled downwardly to disengage the teeth on trigger 52 from lever 48. Release of lever 48 allows biasing member 26 to move forward whereby engagement members 40 move inwardly to their contracted position allowing tool 20 to be removed from implant 22. This method of releasing tool 20 from implant 22 imparts limited forces to implant 22 and does not require any differential torque to be applied between tool 20 and implant 22 which might potentially disturb the positioning of implant 22 in the intramedullary canal into which it has been inserted.

A second embodiment of the present invention is illustrated in FIGS. 6–11. As can be seen in FIG. 6, tool 60 includes a tool body 62 having a shaft portion 64 and a handle portion 66. Tool 60 and its individual parts function similar to tool 20 and its similarly named parts and the discussion of tool 60 is limited to lessen redundancy.

Tool 60 includes a biasing member 68 disposed along a central axis 74 and having a radially enlarged portion 70 located at its distal end 74. Tool 60 also includes a collet 74 having a plurality of engagement members 76 extending from collar portion 80. Relief cuts 78 separate the adjacent engagement members 76. Although not clearly evident in FIG. 10, engagement members 76 define a non-circular cross sectional shape when in a contracted position. Collet 74 is single unitary piece and is secured to the shaft portion 62 of tool body 62 with threaded fasteners 82. Collet 74 also defines an impact surface 92 which is positioned substantially transverse to central axis 74 and located proximate the fixed ends 75 of engagement members 76.

With reference to FIGS. 9 and 11, engagement members 76 define a central opening 84 in which biasing member 68 is disposed. Engagement members 76 define a first inner circumference of central opening 84 at a first axial location as shown by dashed line 86 and a second inner circumference of central opening 84 at a second axial location as shown by dashed line 88. The first inner circumference 86 is located proximate free ends 77 of engagement members 76 and is larger than the second inner circumference 88 which is located between the first inner circumference 86 and fixed ends 75 of engagement members 76. Engagement members 76 define an inclined surface 90 which extends between first inner circumference 86 and second inner circumference 88.

Radially enlarged portion 70 is axially disposed proximate first inner circumference 86 when biasing member 68 is disposed in a position which allows engagement members 76 to assume a contracted position as shown in FIG. 9. In this position, inclined surfaces 71 and 90, which face in opposite directions and are positioned at a common angle to central axis 74, are positioned adjacent to each other. Rearward axial translation of biasing member 68 moves radially enlarged portion 70 to a second position where the inclined surface 71 defining the exterior of portion 70 is biasingly engaged with inclined surface 90 at second inner circumference 88 and thereby deflects engagement members 76 outwardly into an expanded position. Although inclined surfaces 71 and 90 are angled so that rearward movement of biasing member 68 results in the outward deflection of members 76, alternative embodiments could employ differently configured surfaces whereby forward movement of biasing member 68 would cause the outward deflection of engagement members 76.

A ratcheting and leverage mechanism is used to retract biasing member 68 rearwardly. The mechanism includes an external grip 94 which can be pulled towards handle portion 66 resulting in the retraction of biasing member 68. As grip 94 moves rearwardly, rod 96 is also retracted. Rod 96 is secured to T-shaped guide 98 which is limited to linear translation by pins 100. A pivot pin 102 located on guide 98 pivotally secures guide 98 to lever arm 104. As lever arm 104 is pulled rearwardly by its pivot connection to guide 98 it pivots about pin 106 and thereby retracts biasing member 68 which is secured to lever arm 104 by pin 108. Rod 96 also projects rearwardly of grip 94 into handle portion 66. That portion of rod 96 located in handle portion 66 includes teeth which can be engaged to prevent the forward movement of rod 96 (i.e., movement towards collet 74). A spring biased engagement member (not shown) oriented transverse to rod 96 is used to engage the teeth on rod 96. A release button 110 disengages rod 96 and allows spring 112 to bias rod 96 forwardly and place engagement members 76 in their contracted position.

While this invention has been described as having an exemplary design, the present invention may be further modified within the spirit and scope of this disclosure. This application is therefore intended to cover any variations, uses, or adaptations of the invention using its general principles.

What is claimed is:

1. In combination:
    an orthopedic implant having a recess; and
    a tool for gripping the orthopedic implant, comprising:
        a tool body, said tool body including an impaction surface at a proximal end thereof;

a plurality of engagement members circumferentially disposed about a central axis, each of said engagement members having a fixed end secured to said tool body and extending freely to an opposite free end, said plurality of engagement members having a contracted position, said plurality of engagement members having an expanded position wherein at least one of said engagement members is resiliently deflected with said free end of said at least one engagement member displaced radially outwardly relative to said central axis, said fixed ends remaining in the same position relative to said tool body in both said contracted position and said expanded position;

a biasing member biasingly engageable with said at least one engagement member wherein engagement of said biasing member with said at least one engagement member outwardly deflects said at least one engagement member and places said plurality of engagement members into said expanded position; and wherein said plurality of engagement members are adapted for insertion into the recess of the implant when in said contracted position and movement of said plurality of engagement members into said expanded position when positioned in the recess firmly engages said plurality of engagement members with the implant and secures the implant to said tool.

2. The tool of claim 1 wherein, with said plurality of engagement members in said expanded position, each of said plurality of engagement members is resiliently deflected with said free end of each of said engagement members displaced radially outwardly relative to said central axis, said fixed ends remaining in the same position relative to said tool body in both said contracted and said expanded positions.

3. The tool of claim 1 further comprising an impact surface positioned substantially transverse to said central axis and disposed proximate said engagement members, said impact surface adapted to transfer an impact force to the implant when said plurality of engagement members secure the implant to said tool.

4. The tool of claim 1 wherein said plurality of engagement members comprise a single integral part comprising a collar portion encircling said central axis and secured to said tool body, each of said fixed ends integrally joined with said collar portion.

5. The tool of claim 1 wherein said biasing member is an elongate member having a radially enlarged portion at one end, said biasing member disposed along said central axis with said radially enlarged portion disposed between said engagement members wherein positioning a distal end of said radially enlarged portion proximate said free ends places said engagement members in said contracted position and movement of said distal end from a position proximate said free ends towards said fixed ends biasingly engages said radially enlarged portion with said engagement members and resiliently deflects each of said engagement members with each of said free ends being displaced radially outwardly whereby said engagement members are placed in said expanded position.

6. The tool of claim 1 wherein each of said plurality of engagement members is resiliently deflectable and said engagement members define a non-circular cross sectional shape when in said contracted position.

7. In combination:

an orthopedic implant having a recess; and a tool for gripping the orthopedic implant, comprising:

a tool body, said tool body including an impaction surface at a proximal end thereof;

a plurality of engagement members circumferentially adjacently disposed about a central axis, each of said engagement members having a fixed end secured to said tool body and extending freely to an opposite free end, said plurality of engagement members having a contracted position, said plurality of engagement members having an expanded position wherein each of said engagement members is resiliently deflected with each of said free ends displaced radially outwardly relative to said central axis;

a biasing member moveable relative to said plurality of engagement members from a first position wherein at least a portion of said biasing member is disposed along said central axis at a first axial location with said plurality of engagement members in said contracted position to a second position wherein said biasing member is engaged with said plurality of engagement members and resiliently deflects said plurality of engagement members into said expanded position; and wherein said plurality of engagement members are adapted for insertion into the recess of the implant when in said contracted position and movement of said plurality of engagement members into said expanded position when positioned in the recess firmly engages said plurality of engagement members with the implant and secures the implant to said tool.

8. The tool of claim 7 wherein said biasing member is an elongate member disposed along said central axis and having a radially enlarged portion and movement of said biasing member from said first position to said second position includes the axial translation of said radially enlarged portion and biasing engagement of said radially enlarged portion with said plurality of engagement members.

9. The tool of claim 7 further comprising an impact surface positioned substantially transverse to said central axis and disposed proximate said engagement members, said impact surface adapted to transfer an impact force to the implant when said plurality of engagement members secure the implant to said tool.

10. The tool of claim 7 wherein said plurality of engagement members comprise a single integral part comprising a collar portion encircling said central axis and secured to said tool body, each of said fixed ends integrally joined with said collar portion.

11. The tool of claim 7 wherein said plurality of engagement members define a non-circular cross sectional shape when in said contracted position.

* * * * *